United States Patent [19]

Ebner

[11] Patent Number: 5,888,791
[45] Date of Patent: Mar. 30, 1999

[54] **METHOD OF PRODUCING BACTERIORHODOPSIN AND CAROTENOIDS BY ELECTROSTATIC TREATMENT OF *HALOBACTERIUM HALOBIUM***

[75] Inventor: Guido Ebner, Eiken, Switzerland

[73] Assignee: IPR Institute for Pharmaceutical Research AG, Riehen, Switzerland

[21] Appl. No.: 784,239

[22] Filed: Jan. 15, 1997

[30] Foreign Application Priority Data

Jan. 31, 1996 [CH] Switzerland ........................ 00245/96
Jan. 31, 1996 [CH] Switzerland ........................ 00246/96

[51] Int. Cl.$^6$ .................................................. C12N 13/00
[52] U.S. Cl. ...................... 435/173.8; 435/173.1
[58] Field of Search ............................. 435/173.8, 173.1

[56] References Cited

U.S. PATENT DOCUMENTS 4,886,593 12/1989 Gibbs ........................................ 204/667
5,048,458 9/1991 Ebner et al. ............................... 119/3

FOREIGN PATENT DOCUMENTS 4027284 8/1990 Germany .
552353 5/1977 U.S.S.R. .

OTHER PUBLICATIONS

Gillisen et al., Experientia, 8(9), "Der Einfluss von Wechselströmen Verschiedener Stärke auf die Antibiotikaproducktion durch Schimmelpilze in Oberfläschenkulturen", pp. 344–345, 1952.
Stoeckenius (1980) Accts. Chem. Res., 13(10), "Purple Membrane of Halobacteria: A New Light–energy Converter", pp. 337–344.
McGillivray et al. (1986) J. Gen. Microbiol., 132(9), "Applied Electical Fields Polarize the Growth of Mycelial Fungi", pp. 2515–2525.
Gow et al. (1986) J. Gen. Microbiol., 130(11), "Growing Hyphae of *Achlya bisexualis* Generate a Longtitudinal pH Gradient in the Surrounding Medium", pp. 2967–2974.
Eckes P., G., Wengenmeyer F "Genetic Engineering with Plants" Angew. Chem. Int. Ed. Engl. 26 (1987) 382–402.
Goodman R., Henderson A.S. "Sine Waves Enhance Cellular Transcription" Bioelectromagnetics 7; (1986) 23–29.

*Primary Examiner*—Jon P. Weber
*Attorney, Agent, or Firm*—Pennie & Edmonds LLP

[57] ABSTRACT

A method is presented for producing bacteriorhodopsin and carotenoids as secondary metabolites by electrostatic treatment of *Halobacterium halobium* so as to stabilize stress variants of the halobacteria. The metabolites so produced can be harvested from the cell culture medium or a lysate of the halobacteria.

11 Claims, 1 Drawing Sheet

METHOD OF PRODUCING BACTERIORHODOPSIN AND CAROTENOIDS BY ELECTROSTATIC TREATMENT OF *HALOBACTERIUM HALOBIUM*

INTRODUCTION

The present invention describes a novel process, which based on a modification of chemical/physical process procedures in simple as well as in complex systems leads to desirable and useful changes of properties inherent in these systems.

An essential aspect of this invention is concerned with the modification of chemical/physical process procedures in complex biological systems, which manifests itself in a desirable and useful change of certain properties of the organisms present in these systems, such as e.g. a change of the pattern of gene expression, the morphology, the development and growth efficiency, the stress susceptibility asf.

Also comprised by the present invention are therefore organisms, such as e.g. micro-organisms, fungi, plants, invertebrate animals and vertebrate animals from the classes amphibia, reptiles, birds and mammals, which due to the process of the invention possess certain desirable and useful changes, such as e.g. an increased development and growth efficiency, a changed gene expression, a changed morphology, an increased stress resistance, a changed population dynamic asf.

BACKGROUND OF THE INVENTION

The interest concerning investigation of parameters which exert an indirect or direct effect on chemical/physical process procedures has hitherto almost exclusively concentrated on the influence of temperature, pressure and electromagnetic radiation. However, much less attention was paid to e.g. the investigation on possible interactions between simple and complex systems, in particular between complex biological systems and physical fields.

Only in recent times reports have accumulated on possible effects of gravitation and magnetic fields on biological systems. For instance, Goodman and Henderson (Bioelectromagnetics, 1986, 7, 23–29) could find indications for a relationship between electromagnetic fields and the transcription rate in biological material, which are positively influenced by the applied electromagnetic field, and this in the sense of a transcription increase.

However, the possibility that also static electro fields can exert an influence on chemical/physical process procedures in simple or in complex systems, in particular also in complex biological systems, was hitherto apparently excluded from the beginning. Accordingly, up to now no reports exist on a possible effect of static electro fields on said systems. This may primarily seem to be founded on the hypothesis hitherto at hand, which based on the idea that a static electro field in a medium filled with electrical charge carriers would be blocked off by the spontaneous formation of an electrical double layer and would therefore remain inert concerning its effect.

A single exception is an improved pisciculture process described in U.S. Pat. No. 5,048,458. Based on this prior art, however, it could not be expected, according to the generally valid opinion, that this process could be framed into a general method.

This opinion is essentially based on the relation posed by C. Gouy and D. L. Chapman, according to which the effective thickness of a diffuse double layer for an electrolyte is $$d = \frac{1}{F} \cdot \sqrt{\frac{1000 \, \epsilon \, RT}{4 \pi \Sigma c_i z_i^2}}$$

wherein d=the thickness of the double layer, F=the Faraday constant, $\epsilon$=the dielectricity constant, R=the universal gas constant, T=the absolute temperature and i=the ionic species of the concentrations $c_i$ and the valences $z_i$.

SUMMARY OF THE INVENTION

Within the scope of the present invention this prejudice could now surprisingly be overcome by the use of simple process measures. Contrary to what was earlier believed, it has within the scope of the present invention for the first time become possible to develop a process, with the aid of which, based on a modification of chemical/physical process procedures, by the influence of a static electro field in simple as well as in complex systems, in particular in complex biological systems, to induce desirable and useful changes. This can easiest be obtained in that said systems are introduced into a static electro field so that the chemical/physical processes which are to be influenced proceed under the influence of a defined electrostatic field under controllable conditions.

DETAILED DESCRIPTION OF THE INVENTION

Figure 1:
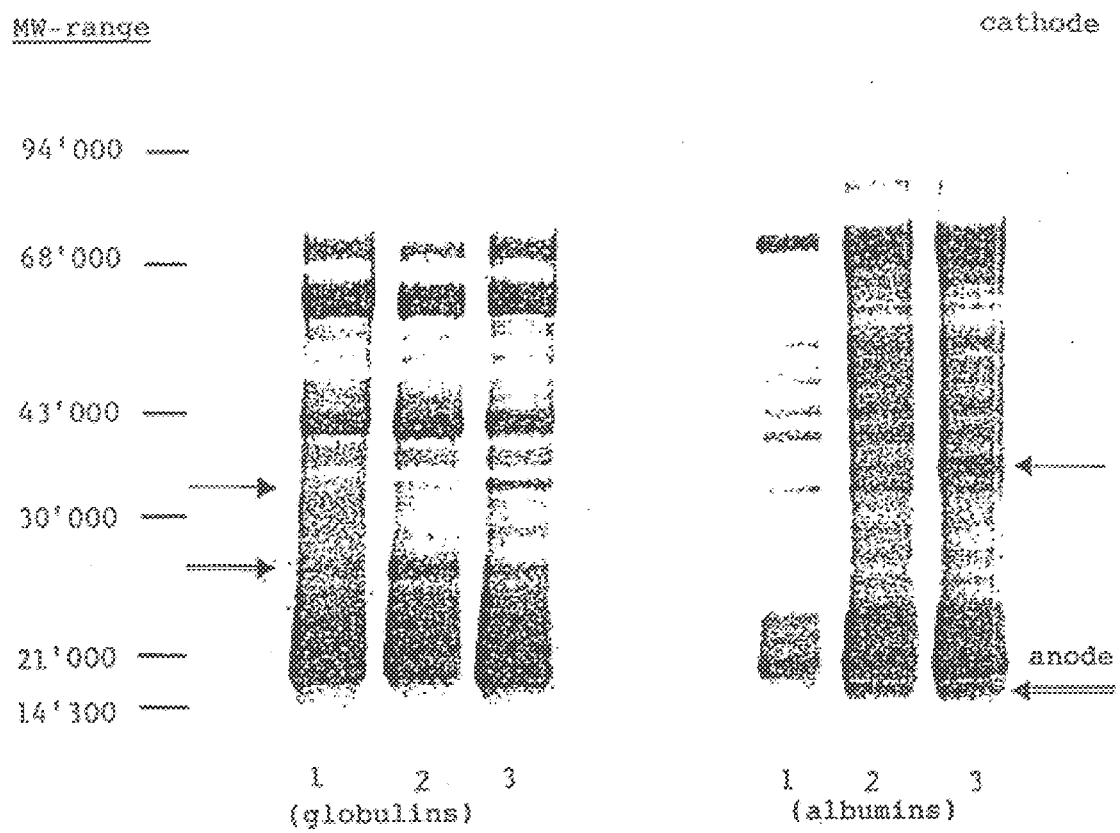
FIG. 1. SDS POLYACRYLAMIDE ELECTROPHORESIS GEL OF RAINERI PROTEINS Lane 1: the control; Lane 2: the grains from the principal sprout; Lane 3: the grains from the side sprout.

Thus, the present invention is concerned with a process, which based on a modification of chemical/physical process procedures in simple as well as in complex systems leads to desirable and useful changes of properties inherent in these systems, and which is characterized in that a) said systems are introduced into a static electro field, so that the chemical/physical processes which are to be influenced proceed under the influence of a defined electrostatic field under controllable conditions; however, without changing the chemical identity of the systems themselves, and b) leaving said systems there for a period of time necessary for a stable formation of the required modification.

The simple and complex systems, which are modified within the scope of the present invention in desirable and useful manner, can primarily cover physical/chemical systems, such as e.g. chromatographic systems, membrane permeabilities, viscosities, solubilities, kinetics of chemical reactions, ionic activities, crystallizations, precipitations, conformations of molecules or dielectricity constants. Particularly preferred are complex biological systems as well as in particular the biological material itself contained in these systems.

Particularly preferred within the scope of this invention is therefore the use of the process of the invention on complex biological systems or on organisms containing these systems, which leads to a number of unexpected manifestations which can be utilized in manifold manner, as is evident from the following detailed description.

Thus, the use of the process of the invention on complex biological systems as component of an intact organism leads e.g. to a change of the development and growth efficiency, the morphogenesis, the gene expression pattern, the stress susceptibility, the population composition asf.

An essential aspect of this invention concerns a process for increasing the efficiency of development and growth of biological material. Particularly preferred is a process for increasing the efficiency of development and growth of plants, invertebrate animals and vertebrate animals from the classes amphibia, reptiles, birds and mammals.

Also covered by the present invention is the biological material itself resulting from the use of the process of the invention, in particular the so resulting plants, invertebrate animals and vertebrate animals from the classes of amphibia, reptiles, birds and mammals, which possess an increased development and growth efficiency, as well as progenies of said organisms produced in sexual or asexual manner which possess these novel and characteristic properties of the starting material.

Under increased development and growth efficiency of plants, invertebrate animals and vertebrate animals from the classes of amphibia, reptiles, birds and mammals are understood, within the scope of the present invention, e.g. an increase of the germination rate and the speeds of germination and growth of plants as well as an increase of the birth rate of animals.

Furthermore, the present invention concerns a process for influencing the morphogenesis of biological material, in particular a process for influencing the morphogenesis of plants.

The present invention thus also encompasses biological material and, in particular, plants which have undergone typical changes in their morphology due to a changed morphogenesis. For plants these morphological modifications primarily concern the form and shaping of leaves and stems, the form of growth as well as the entire habitus of the plants.

Also encompassed by the present invention is a process for changing the pattern of gene expression of biological material, particularly a process for changing the pattern of gene expression of plants as well as the material itself resulting from the use of the process of the invention and its progenies.

A further embodiment of the present invention relates to a process which modifies the specific stress reactions of biological material in desirable and useful manner. This desirable modification of the stress reaction can proceed in very different manner dependent upon the biological material used and the reaction on specific stress situations typical for this material. It is e.g. possible to diminish the stress susceptibility of certain organisms by using the process of the invention and so to cultivate the organisms under conditions which would normally be critical for a normal and regular development of said organisms.

Also encompassed by the present invention are therefore organisms, the specific reactions on specific stress parameters of which are modified in desirable and useful manner by the use of the process of the invention, in particular such organisms as possess an increased resistance towards stress.

Particularly encompassed by the present invention are plants, which due to the use of the process of the invention are capable of growing and multiplying outside the growth period which is typical for them, as well as progenies produced from these plants in sexual and asexual manner, which show these novel and characteristic properties of the mother plant.

A further embodiment of the present invention is a process which enables a direct induction of the secondary metabolism of organisms, which possess such secondary metabolism, and which in this manner makes the production of secondary metabolites possible without the use of laborious process measures.

Also encompassed by the present invention are the secondary metabolite-producing organisms manufactured in this manner as well as the compounds produced therefrom.

The present invention is thus concerned with a generally useful process, which based on a modification of chemical/physical process procedures in simple as well as in complex systems leads to desirable and useful changes of properties inherent in these systems, and which is characterized by the following process measures:

a) introduction of simple or complex systems, in which the specific chemical/physical procedures, which are to be modified with the aid of the process of the invention, take place, into a static electro field, b) adjustment of the field parameters suitable for the desired respective modification of the systems present in the static electro field, and c) leaving said systems in the static electro field for a period of time required for the appearance and, if necessary, for the preservation of the desired modification.

Particularly preferred within the scope of the present invention is a process, which based on a modification of chemical/physical process procedures in simple as well as in complex biological systems leads to desirable and useful changes in properties inherent in these systems, and which is characterized by the following process measures:

a) introduction of biological material into a static electro field b) adjustment of the field parameters suitable for the desired respective modification and c) leaving said systems in the static electro field for a period of time required for the appearance and, if necessary, for the preservation of the desired modification Within the scope of the present invention the static electrofield is preferably built up between the plates of a condenser. The electric field strength of the static electro field is given by the following relation:

$$E = \frac{U}{d'}$$

wherein U signifies the voltage difference between the condenser plates and d' is the plate distance. However, the form of the condenser plates is, for the purpose of the present invention, without significance and can be adjusted to the experimental requirements. E.g. a round flask can be used, in which a metal rod has been inserted, and which is outside surrounded by a material suitable for condensers.

The voltage difference U is generated by a high voltage generator. Arbitrary high voltage generators can be used within the scope of this invention; preferred are high voltage generators, which depend on the transformer principle with rectifier. Other suitable voltage sources are e.g. batteries, van der Graff generators and electrifying machines. The voltage is a continuous or a pulsating rectified voltage.

The preferred voltage difference lies between 1.0 V (volt) and $10^5$ V, depending on the kind of the systems to be modified. For the use of the process of the invention on biological material there is preferably used a voltage difference of 1 V to 20,000 V, in particular from 100 V to 10,000 V. Quite particularly preferred is a voltage difference of 500 V to 3,000 V.

The plate distance of the condensers is governed by the dimensions of the sample vessel and lies e.g. between 10 Å and 10 m, preferably between 1 cm and 50 cm.

The field strength of the static field can be regulated by the voltage of the high voltage generator at a given plate distance.

Within the scope of the present invention the field strength values amount to between 1 V/cm and 10,000 V/cm, preferably between 50 V/cm and 5,000 V/cm. The preferred range for the field strength, when using the process of the invention on biological material, lies at 50 V/cm and 5,000 V/cm. Quite particularly preferred is a field strength of between 500 V/cm and 2,000 V/cm.

Particularly preferred within the scope of this invention is the use of the process of the invention for modification of biological material.

Biological material is, within the scope of the present invention, by definition an intact living organism, such as as e.g. a micro-organism, a fungus, a plant, an invertebrate animal or a vertebrate animal from the classes of amphia, reptiles, birds or mammals, as well as also viable parts of said organisms, which can be kept for a certain time in culture and which are optionally capable of growing in culture and multiplying there. Under the concept "microorganisms" according to the invention are understood, next to bacterias and viruses, primarily one-to polycellular algae as well as one to polycellular fungi. Viable parts of organisms encompass e.g. protoplasts, haploids, diploids as well as polypoloid cells and tissues, isolated cell organelles such as cell nuclei, mitochondria or chloroplasts, calli, cell aggregates, organs, germ cells (e.g. anthers), zygotes as well as embryos, which are capable of growing in culture and optionally multiplying there. Also human cells are to be mentioned in this connection. When said organisms are plant organisms, viable parts thereof encompass also cell aggregates, calli, organs, seeds, spores, pollen and other plant specific structures.

Particularly preferred within the scope of this invention is biological material, which possesses a high divisional activity and/or is still little differentiated, such as e.g. division active cells, sexual cells during the procedure of fertilization, germ cells, embryonic cells and tissues, embryos, zygotes, seedlings or meristematic cells and tissues.

All these exemplary enumerations serve only to illustrate the present invention and do not limit the scope of the invention in any manner.

A main embodiment of the present invention concerns the use of the process of the invention for phenotypic modification of plants, in particular a process for increasing the germination and growth rate of the biomass and seed production, and for modification of the plant morphology based on a changed morphogenesis as well as, optionally, for modification of the pattern of gene expression of the treated plants.

A further embodiment of this invention concerns the modified plant itself and its progenies as well as all mutants and variants thereof, as far as they possess the corresponding modifications.

Considering the rapid increase of the world population and the higher requirements of food and raw materials connected therewith, the increase of the yield of useful plants as well as the increased production of plant products i.e. the advance in the art of food and medicine, belong to the most urgent tasks of the biological/biotechnological research. In this connection the following essential aspects can e.g. be mentioned:

a) an increase of the resistance of useful plants against adverse soil conditions or against disease and parasites, b) an increased resistance against plant protecting agents such as insecticides, herbicides, fungicides and bactericides, c) and, in particular, a favourable change of the nutrient content or the harvest yield of plants.

Such desirable effects could generally be induced by induction or increased formation of protective compounds, valuable proteins or toxins as well as by intervention in the regulatory circulation of the plant metabolism. This can e.g. be attained by influencing the plant hereditary substance with the aid of traditional breeding processes known per se.

A further possibility for specifically influencing the plant hereditary substance consists in transferring isolated genes which code for novel, useful and desirable properties in whole plants or plant cells with the aid of recently developed processes for genetic modification of higher plants.

Exemplary of the above is the use of the gene transfer process depending on the agrobacterium transformation system (Eckes, P. et al., Angew. Chem. Int. Engl., 1987, 26, 382–402).

All these previously mentioned processes are, however, connected with partly aggravating disadvantages. The traditional breeding processes as a rule proved e.g. to be very time- and cost-intensive, so that in this field only slow and gradual advances in the art are to be expected. Also the use of novel gene technologies on the agro sector for introduction of foreign genetic material in plants and the expectation of novel plants with useful, desirable properties connected therewith, is still connected with numerous and partly unsolved problems. This is true primarily for plants of the order Monocotyledonae, which contains the most part of the culture plants most useful from agro-economical view-point. Of particular interest is the family Gramineae, which encompasses our most important cereal plants such as wheat, barley, rye, oats, maize, rice, millet asf.

It must therefore be considered to be an urgent task to develop processes which provide a fast, efficient and cost-favourable change of certain properties of plants relevant from an agro-economic view point. This task could now, within the scope of this invention, surprisingly be solved with the aid of simple process measures.

An embodiment of the present invention is therefore a process for phenotypic modification of plants in particular of culture plants, as well as, optionally, for modification of the pattern of plant gene expression.

Furthermore, this invention concerns the plant material itself manufactured with the aid of the process of the invention and its progenies as well as all mutants and variants thereof as far as these possess the corresponding modifications. Under progenies are understood, within the scope of this invention, all descendants of the modified biological material produced in sexual or asexual manner, in particular also such descendants as have been regenerated with the aid of regeneration techniques from plant cells or protoplasts and still possess the typical properties of the starting material. Under mutants and variants are understood, within the scope of this invention, all descendants of the modified biologic material, in particular the plant material of the invention, produced by artificial or natural mutagenesis, which still possess the typical properties of the starting material.

In a particular embodiment this invention concerns a process for the manufacture of plants with changed, useful and desirable properties in comparison with the starting material, which is characterized in that the seeds of said plants are introduced into a static electro field and are permitted to germinate there.

The process of the invention is characterized by the following process measures:

a) Introduction of plant material into a static electro field, b) Adjustment of the field parameters suitable for the desired respective modification, c) leaving the plant material in the static electro field for a period of time for the appearance and, if necessary, for the preservation of the desired modification.

The above plant material can per definition be whole plants as also viable parts from plants which can grow in culture and optionally be capable of growing in culture and multiplying there, such as e.g. plant protoplasts, cells, isolated cell organelles such as cell nuclei, mitochondria or chloroplasts, calli, cell aggregates, tissues, organs, germ cells, zygotes or embryos. Particularly preferred within the scope of this invention is plant material which has a high division activity and/or is little differentiated, such as e.g. division active cells, germ cells, embryonic cells and tissues, zygotes, embryos, seedlings, meristematic cells and tissues and others. Particularly preferred for use in the process of the invention are plant embryos, in particular embryos present in the form of seeds, as well as monocellular propagation units present in the form of spores. In addition thereto, also e.g. cell cultures can be used in the process of the invention, in particular cultures of germ path cells, such as e.g. anther-, spike- or microspore-cultures.

The process of the invention is therefore primarily characterized in that a) seeds or spores are introduced into a static electro field, b) said seed or spores are germinated under standardized light, temperature and humidity conditions in the static electro field, and c) the seedlings are removed from the influence of the static electro field, transferred into soil and further cultivated as normal seedlings using known processes of cultivation.

When using seeds or spores the duration of incubation depends decisively on the kind of material used as well as on the field strength values of the static electro field. Preferred is an incubation of plant seed or spores over a period of time of from 0.1 to 360 days, in particular from 2 to 8 days, for seeds and from 1 to 180 days for spores. The seeds or spores in a suitable germination medium, preferably in water, are introduced into the dielectricum of a condenser, the plates of which have previously been loaded with the aid of a high voltage generator.

The preferred field strength values of the static electro field built up in the interior of the condenser lie between 10 V/cm and 10,000 V/cm, preferably between 50 V/cm and 5,000 V/cm. Particularly preferred within the scope of this invention are field strength values of 750 V/cm to 1,500 V/cm.

The efficiency of the chosen field strength is dependent on several factors, such as e.g. on the kind of the selected plant material as well as the germination medium used.

In a specific embodiment of the present invention the seeds of the test plants are germinated over a period of time of from 1 to 7 days in a static electro field in water. The field strength values are in this case between 750 V/cm and 1,500 V/cm. When using spores, such as e.g. fern spores, the germination phase can last longer and take several weeks to months.

The germination is effected preferably under standardized conditions, in particular under standardized light and temperature conditions, in a dark chamber, the interior of which is illuminated by a plant lamp, since the germination of seeds and spores are strongly influenced by light.

Subsequently the germinated seeds or spores are transferred into soil and further cultivated like normal seedlings using cultivation processes known per se.

When using fern spores, the development of the protallium must be awaited before the transfer into soil. The protallium is as a rule fully developed after 12 months. After the fertilization of the protallia, the development of the fern plants commences.

The effects resulting from the process of the invention, which can appear separately or in combination, encompass e.g.

a) increase of the germination rate of the seeds or spores treated in the static electro field b) accelerated growth of the plants obtained from the treated seed/spore material c) increase of the biomass production of the plants obtained from the treated seed/spore material, e.g. by formation of further syncarpies d) increase of the seed yield of the plants obtained from the treated seed/spore material e) change of the morphology of the resulting phenotype of the plants obtained from the treated seed/spore material f) change of the pattern of gene expression of the plants obtained from the treated seed/spore material g) change of the specific life habits of the plants obtained from the treated seed/spore material, e.g. change-over from an annual to a perennial life habit.

These effects are also observed on plant material which has been regenerated under the influence of a static electro field from plant protoplasts, cell-, callus-, tissue- or organ-cultures. In addition to these morphological modifications, a slightly increased regeneration rate is found in comparison to the controls.

The observed modifications can also be transferred onto the progenies of said plant materials.

The phenotypic changes on the plant material treated in the static electro field by use of the process of the invention can be utitilized in manifold manner, e.g. for the development of improved seed corn:

a) Increase of the germination rate and the growth speed can e.g. be utilized for development of plants which are capable of germinating also during insufficient light conditions and which are therefore suitable for an earlier sowing in biological border areas having only a short vegetation period.

b) Plants possessing the properties of progenitors can be used for cross breeding with useful plants in order to compensate for degenerative losses on the genetic level. As an example can be mentioned the development of perennial seed corn from otherwise annual wheat.

c) Plants normally possessing a limited number of syncarpies can be brought to develop considerably more syncarpies. As an example, maize can be brought to develop up to 10 instead of 1 to 2 cobs. Thus, the yield of produce per cultivated surface unit can be considerably increased.

The earlier described process of the invention is applicable on all plants, in particular also on those from the systematic groups of Angiospermae and Gymnospermae.

Under the Gymnospermae the plants from the class Coniferae are of particular interest. Under the Angiospermae, next to the deciduous trees and shrubs, above all plants of the families Solanaceae, Cruciferae, Compositae, Liliaceae, Vitaceae, Chenopodiaceae, Rutaceae, Bromeliaceae, Rubiaceae, Theaceae, Musaceae, Gramineae or Leguminosae, and here, above all, the family Papilionaceae are of particular interest. Preferred are representatives of the families Solanaceae, Cruciferae, Leguminosae and Gramineae. Particularly preferred are representatives from the family Gramineae, such as e.g. plants to be cultivated on large surfaces and to yield high produce. As examples are mentioned: maize, rice, wheat, barley, rye, oats, millet, Sorghum asf.; however, without limiting the scope of the invention in any manner.

As possible target cultures for use of the process of the invention there can be mentioned e.g. plants of the genuses Allium, Avena, Hordeum, Oryzae, Passicum, Saccharum, Secale, Setaria, Sorghum, Triticum, Zea, Musa, Cocos, Phoenix and Elaeis; however, without limiting the scope of the invention in any manner.

The process of the invention is, however, not limited to use in plants but can in analogous manner also be used for increasing the efficiency of growth and development e.g. of invertebrate animals and vertebrate animals from the classes amphibia, reptiles, birds and mammals.

A further embodiment of the present invention concerns the use of the process of the invention for modifying specific stress reactions of biological material. Particularly preferred areas of use concern the increase of the stress resistance towards certain environmental factors, such as increased salt concentration in culture medium, limitation of essential nutrients, limitation of light and/or $O_2/CO_2$ supply and others.

One of the most common stress factors in the living environment is the deficiency stress, one or more factors simultaneously acting limiting for a given organism. Deficiency stress appears as soon as one or more of the factors necessary for optimal growth or optimal development such as light, $O_2/CO_2$ supply, nutrient supply, vitamins etc. reach sub-optimal values. This has the result that the organism concerned can no longer to the full extent maintain the synthesis performance necessary for optimal development and optimal growth, which initially leads to a retardation of growth. If the deficiency stress persists over a longer period of time, this finally leads to an impairment of essential life functions, which in the end as a rule leads to a premature beginning of the senescence and thus to death of the organism in question. This is e.g. observed in wheat germ seedlings, where a strong reduction in the light supply leads to browning of the buds and finally to death of the germ seedlings.

The same observations can be made in green algae colonies maintained in culture, which after a reduction of the light intensity over a longer period of time also react with a brown-dyeing. This brown dyeing results from the oxidative degradation of the chorophyll which can no longer be replaced by resynthesis.

Within the scope of the present invention it has now surprisingly become possible to increase the stress resistance of biological material, in particular the stress resistance of bacteria and plants, in that said material is introduced using the process of the invention, into a static electro field and left there for a period of time required for the formation and, if necessary, for the preservation of said stress resistance.

The field parameters are to a certain extent dependent on the biological material used. The field strength units preferably lie at 50 V/cm to 5,000 V/cm, particularly preferred are field strength units of 500 V/cm to 1,500 V/cm.

By using the process of the invention it is e.g. possible to retard the beginning of senescence as a reaction on deficiency stress.

Wheat germ seedlings as well as algae cultures which grow at sub-optimal illumination intensities in the presence of a static electro field show e.g. significantly increased survival rates in comparison to controlled plants without electro field.

A further possibility of use of the process of the invention is the increase of tolerance of biological material, particularly bacteria, towards increased salt concentrations in the surrounding medium.

Not only a deficiency but also an excessive supply of certain critical factors can lead to release of stress reactions. High salt concentration in the nutrient medium, for instance, leads to an increase of the osmotic value in the medium and consequently to a fluid loss of the cells contained therein due to a beginning osmosis and therefore shrivelling of the cells. The fluid loss can as a rule be compensated by corresponding measures of the organisms themselves to a certain extent. However, if a critical treshold value has been exceeded, this will lead to death of the cells concerned.

Within the scope of the present invention it is now surprisingly possible to increase the salt tolerance of living cells in that said cells are adapted stepwise to high salt concentrations in the presence of a static electro field.

The field parameters suitable for a successful adaptation are to a certain extent dependent on the biological material used. Preferred are field strength values between 500 V/cm and 2,000 V/cm, particularly between 750 V/cm and 1,500 V/cm.

The effectiveness of the process of the invention can e.g. be demonstrated on ubiquitous bacteria which can be stepwise adapted to high salt concentrations in the surrounding medium; however, without limiting the invention in any manner. In this manner it is easily possible to accustom ubiquitous bacterias in a first adaptation step to salt concentrations of up to 14% by use of the process of the invention. In a second adaptation step even adaptations to salt concentrations of up to 28% can be attained in the static electro field. In comparison, control cultures, which are adapted to high salt concentration outside a static electro field can only be adapted to up to 3.5% within the same period of time.

The possibilities for fast adaptation of ubiquitously present bacteria to high salt concentrations with the aid of the process of the invention is of great technical interest. As an example, rapidly changing salt concentrations in the biological step of purification plants constitute a long known and hitherto largely unsolved problem, which can now, with the aid of the process of the invention, be solved in simple and efficient manner.

A further phenomenon, which stands in immediate connection with a deficiency stress and which is accessible to a modification by the process of the invention, is the regulation of the secondary metabolism of bacteria and fungi.

It is known that many bacteria and fungi stop their growth when deficiency conditions occur, such as e.g. a limitation of nutrients in the medium or an $O_2$ limitation etc., or at least strongly reduce their growth and change over their metabolism on the production of so-called secondary metabolites. Such secondary metabolites are often compounds with high pharmacological activity such as e.g. antibiotically, antifungicidally or cytotoxically active substances, which are of great commercial interest.

The manufacture of these compounds in sufficient amount within the frame of large-scale fermentation processes is often connected with enormous difficulties and therefore frequently realizable only with great expenditure. The main problem is in this connection the steering of the process parameters, which must be effected in a manner so that the producing strain finds optimal conditions for the manufacture of the desired product.

A relevant example for the use of the process of the invention concerns the cultivation of rhodopsin and β-carotin forming halobacteria. Bacteriorhodopsin enjoys worldwide interest as potential $K^+/Na^+$-pump on the one hand and on the other hand as preferred means of development of biological chips. β-Carotin is similarly of interest as natural product and starting material for vitamin A in biology and medicine. The analysis of halobacteria has yielded, next to rhodopsin and β-carotin, also vitamin A acid, preferably 13-cis-vitamin A acid, and benzaldehyde. Clinical tests on psoriasis patients have in addition revealed that diseased skin areas which are treated with a lysate of *Halobacterium halobium* heal completely.

Therefore, extensive efforts have been made to cultivate the rhodopsin and β-carotin forming form of *Halobacterium halobium* in larger scale. Therefor the bacterium is normally cultivated in its naturally appearing variant. In so doing, high illumination intensities and intensive aeration with oxygen are necessary. If after the multiplication the oxygen supply is strongly limited, it is often possible to cause the normal form of the bacteria to form a purple membrane containing rhodopsin and β-carotin before the population is damaged. In this case the deficiency stress concerning oxygen is the releasing factor for the induction of the rhodopsin syntheses. Within the scope of this invention it is now for the first time possible to stabilize the production variant of a micro-organism capable of producing secondary metabolites, which production variant is normally induced by a deficiency stress ($O_2$ limitation), in that said microorganism is introduced into a static electro field and cultivated in a suitable cultivation medium.

In detail, the process of the invention is characterized in that a) said micro-organism is introduced into a suitable culture medium and b) cultivated in the area of influence of a static electro field c) the cultivation is continued for a period of time until the production form has been formed and stabilized and d) the produced secondary metabolite is isolated from the medium or the cell material.

The choice of the field parameters suitable for the desired stabilization is to a certain extent dependent on the micro-organism used. The preferred field strength values lie between 500 V/cm and 1,500 V/cm, in particular between 500 V/cm and 1,000 V/cm.

Particularly preferred within the scope of this invention is a process for stabilizing the rhodopsin and/or β-carotin forming variant of *Halobacterium halobium*. This can, in accordance with the present invention, be achieved in that bacteria of the normal form of *Halobacterium halobium* in a medium suitable for cultivation of this bacterium are introduced into a static electro field and are cultivated there at weak light for a period of time necessary for the induction and stabilization of the rhodopsin and/or β-carotin forming variant. The field strength of the static electro field chosen for the stabilization of the rhodopsin and/or β-carotin forming variant lies between 500 V/cm and 1,500 V/cm, preferably between 500 V/cm and 1,000 V/cm.

Particular measures for securing a sufficient aeration are in this case not necessary. The use of the process of the invention leads to direct formation of the rhodopsin form, which can be further multiplied in a manner known per se by inoculation of suitable culture media.

The breeding method of halobacteria according to the present invention, in particular of *Halobacterium halobium*, has in comparison to usual methods the advantage that the bacteria multiply faster, that they produce at least 19% to 121% more bacteriorhodopsin and 10% to 30% more biomass in the cell membrane and that they possess a content of vitamin A acid and benzaldehyde. In addition, halobacteria which have previously stabilized their gene expression in the static electro field maintain their contents of bacterio rhodopsin, biomass and vitamin A acid without electrostatic field for about three months. In addition, bacteria which were subjected to the electro field produce partly different metabolites, such as e.g. benzaldehyde.

Subject of the invention is in addition a bacteria lysate, which—as has been described above—is obtained from the halobacteria bred in the static electro field. For obtaining the lysate the bacteria are centrifuged off and osmotically disintegrated in distilled or demineralized water. The resulting solution contains, among others, bacteriorhodopsin, biomass, vitamin A acid and benzaldehyde. Bacteriorhodopsin and benzaldehyde are qualitatively and quantitatively spectroscopically identified. The vitamin A acid is identified chromatografically with the aid of HPLC. The biomass is determined according to the amount of cell proteins with biuret-colour reaction. The bacteria lysate according to the invention contains, in comparison to lysate from the wild type bacteria, 19% to 121%, in particular 50% to 100%; however, at least 19% more bacteriorhodopsin and 10% to 30%, in particular 15% to 25%; however, at least 10% more biomass as well as a content of vitamin A acid and benzaldehyde.

The present invention concerns in addition medicament preparations containing as active ingredient a) halobacteria, in particular *Halobacterium halobium*, or b) standardized lysate of halobacteria, in particular *Halobacterium halobium*, or c) bacteriorhodopsin, vitamin A acid and benzaldehyde, or d) bacteriorhodopsin and a retinoid, or e) bacteriorhodopsin alone.

It is preferable to enrich these medicament preparations with 13-cis-vitamin-A-acid derivatives and/or 13-cis-vitamin-A-aldehyde and/or 13-cis-vitamin A-aldehyde-derivatives and/or 13-cis-vitamin-A-aldehyde-Schiff-bases and/or 13-cis-vitamin-A-aldehyde-acetals and/or anlogues and/or cis-/trans-isomers of the previously named compounds.

Medicament preparations according to the invention are all suitable galenic forms, preferably topical forms such as e.g. gels, solutions, emulsions, ointments, pastes and bath additives; particularly preferred are gels.

The medicament preparations according to the invention contain one or more of the named active ingredients in a concentration of 0.1% to 70%, preferably 0.5% to 50%; particularly preferred is 1% to 10%.

Medicament preparations according to the invention with a standardized bacteria lysate of 2% (see example 6.5.) can be further processed, and therefrom—relating to a starting concentration of 2%—medicament preparations with a concentration of 0.1% to 99%, preferably 25% to 75%, particularly preferred 50%, can be manufactured.

For the manufacture of topical medicament preparations aqueous solutions of the bacteria lysates are suitable which are either applied onto the skin or used as bath additive. The lysate can also be processed to gels with hydrophile macromolecular compounds such as e.g. gelatine and cellulose ether, to emulsions, with the use of oil, gum arabic and water, to a hydrophile ointment base, e.g. macrogol or polyethyleneglycol ointment, to creams containing hydrophobe lipid constituents, water and tensides, to pastes from a highly concentrated suspension ointment. The manufacture of these topical medicaments proceeds according to conventional methods.

The present invention in addition encompasses the use of the medicament preparations of the invention for combatting skin diseases, particularly hyperkeratotic diseases, in particular psoriasis.

Among the medicaments of the prior art numerous topical and oral medicaments for treatment of psoriasis are available. These medicaments only offer symptomatic alleviation of the complaints as long-time therapeutics, they are mostly connected with side-effects, and when interrupting the treatment, the condition of the patient worsens within a short time.

The present invention bases on the task to develop medicaments which completely heal psoriasis or at least guarantee a long time free of complaints, and are free of, or low in side-effects.

In pre-assays psoriasis patients were in accordance with the invention treated with a 2% lysate of *Halobacterium halobium*. Several scale areas were brushed with the bacteria lysate and subsequently subjected to irradiation with a 300 watt lamp. During this time the skin areas were brushed further five to six times with the bacteria lysate. The treatment was continued daily over a period of time of 200 days. In comparison to untreated controls the treated skin areas healed completely and, also after six years, did not form any relapses.

The medicament preparations according to the invention are generally utilized for combatting skin diseases, particularly hyperkeratotic processes, in particular psoriasis. For treatment of psoriasis the medicament preparation is applied twice to three times daily on the skin areas under concern; when required, the skin areas can subsequent to the application of the medicament preparation be irradiated with a 300 watt lamp during 20 to 60 minutes, preferably during 40 minutes. The use of UV irradiation, which is damaging to skin, such as is usually employed as auxiliary therapy of psoriasis, becomes superfluous.

The use of the process of the invention leads to a further phenomenon which is of importance for practical use. By evaporation of the water in the culture dishes sodium chloride crystals develop, in which rhodopsin forming halobacteria are confined. These bacteria surprisingly survive and multiply in the interior of the crystals when the crystal is kept in an electro field. Also a week-long chill period in a deep-freeze cupboard is survived without damage. A subsequent culture is possible, when the crystal is dissolved in a nutrient medium.

The same observations are made concerning ubiquitous bacteria which are adapted to high salt concentrations according to the process of the invention, and such bacteria can also be maintained in confinement in salt crystals. The process of the invention is thus in detail characterized in that a) said bacteria are incubated in a highly concentrated salt solution, b) the latter is subsequently introduced into a static electro field c) the solvent is gradually evaporated and d) the bacteria are confined within the crystallizing salt crystals.

In this manner a very simple and—as seen from practical considerations—efficient system for maintenance of halobacterias and for ubiquitous bacteria adapted to high salt concentrations is submitted. For the cultivation and multiplication of these bacteria it is thus sufficient to dissolve salt crystals which contain these bacterias in viable form in a suitable cultivation medium and subsequently to cultivate the bacteria under conditions of cultivation known per se.

A further form of stress is present when different organisms live together in mixed population.

The process of the invention can exert a modifying influence also on this system in that under the influence of a static electro field certain members of a mixed population are promoted in their growth and their development, and can thus better resist the competitive pressure. This in general occurs at the cost of one or more other members of the mixed population.

As an example this can be demonstrated on a bacteria/mixed-culture consisting of *E. coli* 205, *K. pneumoniae* 327, *P. aeruginosa, S. aureus* 10B, *S. pyogenes* L-15 as well as *Bacillus subtilis* MX-1. If this mixed culture is cultivated within the field of influence of a static electro field, significant displacements in the population structure appear, such as e.g a strong increase of *E.coli* at the cost of *K. pneumoniae*.

It is thus possible to significantly change the composition of a mixed population with the aid of the process of the invention, which in practice offers manifold fields of use.

For illustration of the above general description as well as for a better understanding of the present invention, reference is made to the following specific working examples which do not have any limiting character unless this is specifically pronounced. The exemplary enumerations in the preceding description is to be read in the same sense.

NON-LIMITING WORKING EXAMPLES

Arrangement of the static electro field (in the following referred to as "test arrangement")

All tests described in the following are carried out in static electro fields which are arranged between the plates of a condenser.

The electric field strength is given by the relation $$E = \frac{U}{d'}$$

in which U is the voltage difference between the condenser plates and d' is the distance between the plates of the condenser. The voltage is generated with the aid of a high voltage generator which is based on the transformer principle with rectifier, voltage differences of between 500 volt and 12,000 volt as a rule being used. The difference between the plates of the condenser depends on the dimensions of the test vessels used in the different tests. As a rule the variable parameters U and d' are selected so that the static electro field possesses field strength values between 250 V/cm and 1500 V/cm.

1. EXAMPLE

Germination in the static electro field 1.1 Garden Cress

A counted up number of cress seeds (140 seeds per test) is divided out on filter paper in petri dishes, 5 ml of water are added and the dishes are closed with parafilm. During the germination phase (about 5 days) one of the petri dishes stays in the above described "test arrangement" and is subjected to a strong static electro field with a field strength of 750 V/cm. The negatively charged plate of the condenser forms the cover of the test cell. The second petri dish is kept outside the area of influence of the static electro field and serves as control.

In order to exclude an uncontrolled influence of the light on the germination, the test is carried out under standardized light and temperature conditions in a dark chamber, the interior of which is illuminated by a 100 watt plant lamp at a distance of 28 cm to the surfaces of the test cells. The temperature in the dark chamber lies between 23° C. and 24° C.

The germination rate of the cress seeds used is determined after the development of the hypokothyl and the shoots. The germination rate is on average 83% for the seeds germinated in the static electro field. In controls without static electro field, of the same number of seeds only an average of 21% germinates. The subsequent growing in soil at day-light shows that all seeds are capable of germinating in the same manner.

1.2 Wheat

The germination tests with wheat are carried out in the same manner as previously described for cress (see example 1.1.). The wheat type used is a tender wheat (Anza-wheat, Canada) and a hard wheat (Raineri-wheat, Italy). For the tests carried out with wheat the number of the tested seeds amount to 30 per petri dish. 15 ml of water are added thereto in petri dishes, the dishes closed with parafilm and germinated for a period of time of 1 to 7 days in water, the seeds of the test plants being subjected to a strong static electro field. The field strength is 750 V/cm.

The further conditions are standardized as follows:

Illumination strength: 100 watt plant lamp (Osram Concentra R 95 Natura) at a distance of 80 cm corresponding to 133 μwatt/cm².

Temperature: 23° C. to 24° C.

Hard wheat (Raineri)

The germination tests with winter wheat (Raineri) make it evident that the germination rate as well as the number and length of the roots and also the length of the epikothyl increase strongly in comparison to controls under the influence of a static electro field (see table 1). The continuation of the test shows that this advantage remains also after the sowing until the ripeness of the plants.

Table 1

Comparison of the germination and growth efficiency of wheat seeds (Raineri) treated or not in a static electro field:

|  | without e-field | with e-field | Δ% |
| --- | --- | --- | --- |
| germination | 19 | 26 | 137% |
| number of roots | 106 | 137 | 129% |
| length of roots (mm) | 112 | 188 | 168% |
| length of epikothyl (mm) | 222 | 296 | 133% |

Comparison between Anza wheat and Raineri wheat

Anza wheat (soft wheat, Canada) and Raineri wheat (hard wheat, Italy) behave in differentiated manner.

Table 2

Comparison of the influence of a static electro field on seeds of Anza wheat and Raineri wheat:

|  | Anza wheat | | | Raineri wheat | | |
| --- | --- | --- | --- | --- | --- | --- |
|  | without e-field | with e-field | Δ% | without e-field | with e-field | Δ% |
| germination | 2 | 2 | 100% | 3 | 4 | 133% |
| number of roots | 7 | 8 | 114% | 11 | 15 | 136% |
| length of roots (mm) | 140 | 160 | 114% | 140 | 380 | 270% |
| length of epikothyl (mm) | 220 | 170 | 80% | 110 | 490 | 460% |

Anza wheat is considerably less favoured: The germination and the root growth remain about the same; the epikothyl is rather inhibited (cf. table 2). In a field test was shown that Anza wheat germinated in an electro field in the starting phase grows faster than that without electro field; however, up to ripeness the differences disappear. Nevertheless, in general the conclusion can be made from this investigation that an electro field influences the germination rate as well as also the growth behaviour.

1.3 Maize

Analoguous to the procedure described in example 1.2. for wheat 10 seeds of the maize type FMI A 188 are brought to germination in a static electro field at a field strength of 1,500 V/cm. After a duration of treatment of 6 days an increased germination rate can also be demonstrated for the samples treated in the static electro field in comparison to the controls.

Table 3a:

Comparison of germination- and growth-efficiency of maize seed treated in a static electro field with untreated maize seeds:

|  | without e-field | without e-field |
| --- | --- | --- |
| germination | 16 | 20 |
| length of epikothyl (mm) | 0 | 30 |

The seeds pre-germinated in the manner described are subsequently transferred to standardized soil [40% land soil, 50% peat (TSK-1;"Floratorf"), 10% sand] in 5 l pots and further grown as normal seedlings. Already after 4 days it is possible to discern distinct differences in emergence behaviour and growth speed between control and test plants.

Table 3b:

Differences in emergence behaviour and growth speed between treated and untreated maize seedlings.

|  | without e-field | without e-field |
| --- | --- | --- |
| emergence | 9 | 20 |
| formation of leaves | 1–2 | 3–4 |

2. EXAMPLE

Morphologic changes

Adult plants produced from seeds germinated in a static electro field under the previously described conditions partly show considerable morphologic changes in comparison to control plants. These changes are:

a) more stems with more spikes (2 to 7)
b) changed leaf position
c) formation of panicles with a multitude of spikes
d) shrub forms, creeping forms.

2.1. Wheat 5 wheat grains (Raineri) are placed in a petri dish with 10 ml of water. The dish is closed with parafilm strips and germinated in the above described "test arrangement" 8 days at a field strength of 1,500 V/cm. The seedlings are subsequently planted in ½ l pots with sterile field soil and further cultivated in a normal manner (cf. example 1.3.). Already in the germination phase the electro field induces an increased root growth which is reflected in the number and size of the roots formed as well as an increased growth of the epikothyl. After a duration of cultivation of 8 to 10 weeks the planted seedlings show a significantly different morphology in comparison to the control plants:

1. a larger number of stems (6,8 in comparison to 4,8)
2. a larger number of spikes (same difference as for the stems)
3. larger spikes (grain number 38 in comparison to 32)
4. sometimes a habitus appears which resembles the genetic progenitors of wheat: e.g. rough-meadow-grass-like arrangement of small spikes and small narrow leaves.

2.2 Maize 20 maize grains (FMI A 188) are added to a petri dish with 15 ml of water. The dish is closed with parafilm and germinated in the above described "test arrangement" for 8 days at a field strength of 1,500 V/cm. The seedlings, which also show an increased root and epikothyl growth, are subsequently planted into 5 l pots in sterile field soil (cf. example 1.3.) and further cultivated in normal manner in greenhouse. The soil is sprinkled weekly with standard manure (Wuxal, Fa. Maag, CH).

After a duration of cultivation of 14 weeks the seedlings show a significantly different morphology in comparison to the controls:

1. a larger number of cobs per plant (3 to 6 in comparison to 1 to 2)
2. compact habitus in comparison to normal (broad leaves, thick stems)
3. a different positioning of the cobs in comparison to normal (cobs at the upper stem end instead of in the leaf axil)
4. treble cobs in spicate formation, the two side cobs being fully developed after only 5 days, and these cobs form still further cobs
5. formation of more stems.

2.3 Fern

A cellulose fabric ['Lens clean' paper (Spectra Physics)] is put into a petri dish and sprinkled with 2 ml of Evian water [(mineral water, S.A. Des eaux minérales d'Evian, Evian, France)]. On this paper spores of shield fern, which have been produced by beating fern leaves, are applied in large number. The petri dish is closed with parafilm and subjected to a static electro field of 1,500 V/cm in the above described "test arrangement". After 6 to 7 weeks the spores start to germinate and in about 7 months they form a protallium that is fully developed in the 12th month. In this state the plants are transferred into sterile standardized field soil (cf. example 1.3.). To this end the part of the paper containing protallia is cut out and put onto the surface of the soil layer which has been moistened with much water. Within the course of 6 weeks the fertilization takes part on the protallia, and the first fern plants start to develop.

The so formed plants differ morphologically quite significantly from the control plants. The leaves show an entire although strongly folded habitus; a leaf division does not take place. In comparison to normal growth the grouping of the leaves appears centered instead of sweeping.

2.4 Hyoscyamus muticus L

Each 5 anthers of *Hyoscyamus muticus* L are cultivated in 6 cm petri dishes on sterile agar (Nitch, Science, 1969, 163, 85–87). The dishes are sealed in sterile manner with parafilm and cultivated in the above describes "test arrangement" at a field strength of 2,000 V/cm for several weeks. After a duration of cultivation of about 6 weeks the first haploid plants develop.

Also in this case the plants cultivated in the electro field possess a developmental lead in comparison to the controls. Of each 45 anthers in the electro field 15 have at this point of time developed to plants, whereas for the controls this has occurred for only 10.

The plants are now transferred into large closed plastic vessels (diameter 9 cm, height 6 cm) in fresh sterile agar. The plants cultivated in the electro field are continually subjected to an electro field of a strength of 1,500 V/cm. Already now the plants show distinct morphologic differences in that those without electro field form round leaves, whereas those with electro field show lancet formed leaves.

After further 7 weeks the plants are transferred into pots with vermiculite (exfoiled mica, Fa. Vermica AG, Bozen, CH) and further cultivated at a temperature of 26° C. to 27° and a relative humidity of 60% in a climate chamber. The illumination intensity is 10,000 Lux, a day/night rhythm of 12 h day/12 h night is maintained.

The further cultivation of the test plants now proceeds without the influence of a static electro field. After 10 weeks the habitus of the plants cultivated in the electro field has, in comparison to the controls, once more distinctly changed. While the leaves of the controlled plants are positioned in a shrub-like manner, the plants cultivated in the electro field show a leaf stem with whirl-positioned leaves as well as beginning formation of flower buds.

In this state the plants are transferred into normal plant soil moved into greenhouse and further cultivated there. After further 3 months the control plants show a shrub-like habitus with low stem which does not yet carry blossoms. The plants treated in the electro field, however, have three stems. Several plants are already over and carry the onset of syncarpies. The resulting fruit capsules are harvested and the seeds collected. The seeds from untreated plants have normal colour, those cultivated in the electro field are white. The latter is a known indication of haploidy. A further indication of haploidy is, according to Wernike et al. (Plant Scienc. Lett., 1979, 15, 239–249) the number of chloroplasts per leaf cell. The count results in an average of 13 for untreated plants; for test plants, however, an average of 7.8. The plants cultivated in the electro field thus possess predominantly typically haploid features in contrast to the control.

3. EXAMPLE

Changes of growth

In addition to morphologic changes adult plants from seeds which have been germinated under the influence of a static electro field also possess a large variability in their growth behaviour:

a) increased biomass (10 to 100%)
b) increase of yield, divided on several spikes (30 to 120%)

c) strongly accelerated growth with development of a second stem (within 4 week)

d) perennial life habit of the plants resulting from treated seeds.

4. EXAMPLE

Progenies

The seeds of the test plants earlier described remain fully viable, the germination rate lies at 100%. The earlier described morphologic changes as well as the changes in growth behaviour are partly upheld also in the subsequent generation. These plants can therefore be utilized for breeding new and improved plant types (seed corn improvement).

5. EXAMPLE

Change of gene expression

For examination of possible differences in the gene expression of treated plants the protein patterns of wheat grains from control- and test-plants are investigated with the aid of gel-electrophoretic (PAGE) processes (Stegmann H. et al., AGE Manual, 1986; Stegmann H., Z. Anal. Chem., 1970, 252; 165–169). The test plant is a Raineri wheat which due to the germination in the static electro field has, in addition to the normal principal sprout, also developed a side sprout. The protein patterns of grains from the principal sprout as well as from the side sprout are examined, and also control grains from not treated Raineri plants.

5.1 SDS PAGE of the water soluble proteins (albumins)

Wheat grains are ground to flower and extracted with water. The examination of the protein extracts is effected with SDS PAGE.

a) Test solutions incubation

The protein extracts provided for the electrophoretic examination are incubated with SDS and prepared for application as follows:

buffer pH 7.1 1,226 g TRIS buffer 12,366 g boric acid ($H_3BO_3$) dissolved together in water, diluted to 200 ml.

incubation solution: 5% SDS and 5% 2-mercaptoethanol in buffer pH 7,1.

charge: 400 $\mu$l protein extract+100 $\mu$l incubation solution. Mix.

time of incubation: 3 minutes in boiling water bath solution to be applied: about 100 ml of sugar (*Saccharose puriss;* Fluka) and 1 drop of 0.1% aqueous amido-black solution are added to 500 $\mu$l of incubated protein solution and mixed.

application: each 40 $\mu$l.

b) Electrophoresis buffer

TRIS/boric acid pH 7.1: 6.13 g of TRIS buffer 61.83 g of boric acid ($H_3BO_3$) 5.00 g of SDS (Dodecylsulfat-sodium) dissolve together in water, fill up to 5000 ml.

c) Electrophoresis temperature: 0°–2° C.

buffer revolution: is effected voltage and running time: 400 V, 105–120 minutes.

d) Proof

Protein coloration with Coomassie-Brillant Blue R-250. SDS-PAGE of the proteins (globulins) soluble in tris/borate-buffer From the sediment obtained in 5.1 above further proteins (globulins) are extracted with tris/borate buffer and also analyzed with the aid of SDS-PAGE (cf. 5.1).

Clear distinctions, such as e.g. establishment of missing zones or appearance of additional zones or particularly strong intensity differences for the zones, is shown by the SDS-PAGE of the water-soluble and the salt-soluble proteins. These differences are confirmed by repetition of the extractions and repeated examination of all extracts together and are reproduced in FIG. 1. Also for the other tested methods (normal PAGE, esterases, IEF, gliadine) slight intensity differences of individual zones are established.

5.3 Results

SDS-PAGE of the water-soluble proteins (albumins)

The sample of grains from the principal sprout (2) differs from the untreated control by the appearance of its slight additional protein zone in the MW range at 29,000 (←). In the sample of the side sprout (3) this additional zone appears even relatively strongly. In the MW range 13,000 a zone is observed in both samples, which in the sample of the untreated control is missing (⇐).

SDS-PAGE of the proteins (globulins) soluble in TRIS/borate-buffer

Also in this pherogram the most distinct differences are found mainly in the MW-range between 14,000 and 30,000. In the MW range about 28,000 an additional slight zone appears (→) for samples from the test plants (2,3) as for the albumins, and at MW about 24,000 a strong zone is observed in the sample from the principal sprout (2) which in the two remaining samples is only observed to a slight extent (⇨).

6. EXAMPLE

Influence of the static electro field on stress behaviour

6.1 Retarded Start of Senescence for Green Algae

Green algae cultures obtained by smear on algae culture medium in petri dishes are developed at insufficient illumination (133 $\mu$watt/cm$^2$) in the above described "test arrangement". Both at a field strength of 1,500 V/cm and at 750 V/cm the cultures outlive comparative material without electro field. The latter already after 1 month shows a distinct deficiency appearance and is after 2 month brown. In the same period of time cultures cultivated in the electro field develop normally.

6.2 Increased Salt Resistance of Ubiquitous Bacteria

An arbitrary mixture of ubiquitous bacteria from a soil sample is cultivated in petri dishes for 5 days in water at room temperature. From this suspension each 1 ml is inoculated into 6 petri dishes which each contain 15 ml of a diluted sea water medium (cf. table 4; dilution 1:2, 1:4, 1:8). 3 dishes are subjected to the above mentioned "test arrangement" in a static electro field of 1,500 V/cm, the remaining serve as control. After 7 days the dishes in the electro field show a distinct increase of the bacteria population, whereas the control dishes do not show any development. The electro field aids in overcoming the salt stress.

In a second adaptation step bacteria from the culture grown at a dilution of 1:2 in the electro field are removed. These serve as starting material for inoculation onto a further petri dish which now contains the culture medium according to table 4. 1 ml of this suspension is transferred into 15 ml sea water medium and the petri dish again subjected to a static electro field of 1,500 V/cm in the above described "test arrangement". Within 3 weeks the culture develops completely, i.e. until maximum equilibrium population. In this manner a ubiquitous bacteria mixture is adapted from sweet water to a saturated salt solution.

TABLE 4

Sea water culture medium

Salts (amount per 1 liter solution

| | |
|---|---|
| NaOH | 7–8 g |
| NaCl | 250 g |
| KCl | 2 g |
| CaCl$_2$ | 7 mg |
| DL-malonic acid | 15 g |
| Na$_3$-citrat | 0,5 g |
| glycerine | 1 ml |
| casamino acids | 7,5 g |
| phosphate buffer solution | 1 ml |
| vitamins | 1 ml |
| trace elements | 1 ml | dissolve in H$_2$O, additionally add 9 g MgSO$_4$ (anhydrous) and titrate with NaOH to pH 6,8–7,0.

Phosphat buffer solution

| | |
|---|---|
| K$_2$HPO$_4$ | 50 g/l |
| KH$_2$PO$_4$ | 50 g/l |

Vitamin solution

| | |
|---|---|
| folic acid | 100 mg/100 ml |
| thiamine | 100 mg/100 ml |
| biotine | 100 mg/100 ml |

Trace elements

| | |
|---|---|
| ZnSO$_4$ | 44 mg/100 ml |
| MnCl$_2$ | 30 mg/100 ml |
| Fe(ll)Cl$_2$ | 230 mg/100 ml |

6.3 Confinement of Adapted Bacteria Within Sodium Chloride Crystals

If during or after the development of a bacteria culture according to example 6.2 a slight amount of water is evaporated, the sea water solution starts crystallizing. If this process proceeds in the static electrofield according to the above described "test arrangement", primarily sodium chloride crystallizes out. In distinction to the normal crystal form of a cube, however, octahedrons with a body axis in the direction of the electro field are formed. Within the interior of such a crystal bacterias are confined. These are partly fully confined by salt, partly they exist in chambers, in which they maintain their mobility and life activity over several years. In addition, they are capable of expanding the chambers in order to multiply. In this form they can also survive a chill shock at −35° C. over weeks without damage. If the crystals are subsequently, or even after years, redis-solved in sea water or in another suitable medium, they prove to be fully vital.

6.4 Halobacteria—Formation of the Rhodopsin Form

Halobacteria exist in two forms, one normal form and one rhodopsin-forming form, which is required as producer of rhodopsin and β-carotin.

A strain of normal Halobacteria (*Halobacterium halobium*—wild type HHBM, Rechovot, Israel) serves as starting material for inoculation of 20 ml of a sea inoculation material 100 μl of a stock solution is used containing 50 mg of Halobacteria per 10 ml of sea water medium. The test vessels are introduced into a static electro field and incubated there at field strength values between 750 V/cm and 1,500 V/cm at an illumination strength of 130 μw/cm$^{-2}$. Under these conditions the Halobacteria form the rhodopsin form within 8 to 14 days and start with the production of rhodopsin and β-carotin. After 3 to 4 weeks a saturated population of Halobacteria with purple membrane is formed. Onto this stock solution culture flasks can continually be inoculated. 100 μl of the described stock solution and 500 ml of sea water are required. The flasks are closed with parafilm—i.e. not closed with the lid—and incubated standing vertically in the above described "test arrangement" at room temperature and 750 V/cm. After 6 weeks a maximum equilibrium population is attained. Therefrom rhodopsin can be obtained in a manner known per se by centrifuging off the bacteria and subsequent recovery in distilled water. The process can also be managed in continuous manner. To that end the solution saturated with bacteria at the bottom of the vessel is sucked off, and the same amount of fresh sea water is added at the same time at the top. In larger apparatuses the addition of slight amounts of air is recommended.

Proof of the rhodopsin form

As proof that under the field conditions the rhodopsin form has indeed been formed directly, the bacteria cultures are centrifuged off and the so-obtained bacteria cells resuspended in distilled water. This leads to lysis of the bacteria cells and to liberation of rhodopsin and β-carotin. The rhodopsin and β-carotin liberated in this manner from the cells can be identified with the aid of spectroscopic procedures.

6.5 Standardized Bacteria Lysate 2% for Treatment of Skin Diseases

Manufacture of the standardized bacteria lysate 2%: 0.5 liters of nutrient solution containing the *Halobacterium halobium* of the invention are centrifuged 25 minutes at 5,500 rpm. To the bacteria pellet obtained a corresponding amount of dimineralized water is added so that a 2% bacteria lysate solution is formed. The bacteria lysate is stirred with magnetic stirrer at 700 rpm until the solution is homogenous (about 10 min.).

6.6 Bacteria Lysate gel 50% for Treatment of Skin Diseases

Composition for 100 g gel:

| | |
|---|---|
| standardized bacteria lysate 2% | 50,0 g |
| Na-carboxymethylcellulose (carbopol 980) | 1,5 g |
| Isopropyl myristate | 5,0 g |
| Polysorbate 80 | 5,0 g |
| Isopropanol | 30,0 g |
| Tromethamine 1M | 7,5 g |

Charge 1: Keep 50 g of standardized bacteria lysate 2% homogenous on the magnetic stirrer at 700 rpm. Add gradually Na-Carboxymethylcellulose with stirring and mix well (about 10 minutes). Subsequently swell for 30 minutes.

Charge 2: Isopropyl myristate, polysorbate 80 und Isopropanol are weight off and mixed in a beaker with magnetic stirrer at 700 rpm.

Finishing of the gel: Charge 2 is added to charge 1 and mixed with magnetic stirrer at 700 rpm until the gel is homogenous. With continuous stirring the gel is titrated with 1M tromethamine until a pH-value of 6–7.

6.7 Confinement of the Rhodopsin Form of *Halobacterium halobium* Within Salt Crystals Slow evaporation of the water in the electro field from a solution of sea water saturated with bacteria leads to crystallization of sodium chloride crystals. They contain live bacteria material. The crystals can be dried. When the halobacteria are introduced into an electro field of 750 V/cm, they can survive several years enclosed in the crystal. They even multiply. After dissolution of the crystal in new sea water the bacteria are fully viable. Also Halobacteria which are enclosed in the salt and stored in the deep freeze—without electro field—over a longer time (more than 1 month) at −28° C. remain fully viable.

6.8 Effect of a Static Electro Field on the Composition and the Growth of a Mixed Bacteria Population

*E. coli* 205K, *K. pneumoniae* 327, *P. aeruginosa* ATCC12055, *S. aureus* 10 B, *S. pyogenes* L-15 and *Bacillus subtilis* MX-1 are bred under aerobic conditions over-night at a temperature of 37° C. in Brain Heart Infusion (BHI) medium (Difco Manual, 10th Edition, Difco Laboratories Inc., Detroit, Mich., 1984, 160–162). *C. perfringens* is bred over-night under anaerobic conditions on BHI-agar at a temperature of 37° C., and the colonies obtained resuspended in BHI culture medium.

The over-night cultures are diluted in BHI-medium until the suspension just about appears turbid to the eye. Each 1 ml of the so-prepared suspensions is added to 13 ml of a pre-heated fresh BHI-culture solution, so that a total volume of 20 ml results.

The mixed cultures are transferred into 25 cm³ tissue culture flasks, two of the flasks are incubated in a static electro field, whereas two further flasks serve as controls. The incubation proceeds at a temperature of 37° C. while the cultures are shaken three times per day. Samples are taken daily and plated out in suitable dilution (giving about 200 colonies per plate) on eosin-methylene-blue-agar (for differentiation of *E. coli, K pneumoniae* and *B. subtilis*) [Difco Manual, page 307–308], on mannitol-salt agar (*S. aureus*) [Difco Manual, page 588–560], Pseudomonas selection agar (*P. aeruginosa*) [Difco Manual, page 709–711], blood agar (2×, 1. aerobic for *S. pyogenes;* 2. anaerobic for *C. perfringens*). These media permit the determination of the number of the single components of the mixed cultures.

Result

The static electro field has no influence on the total number of the organisms in the mixed cultures. However, the results in table 6 show that the interactions between the different components of the mixed culture are influenced by the electro field and lead to an increase of different species in the mixed population. This occurs as a rule at the cost of one or more other species present in the mixed culture. As an example, the proportion of *P. aeruginosa* 24 hours after start of the test under field conditions is slightly higher than the controls. This increase occurs at the cost of *E. coli,* which is present at a higher percentage in control cultures than in the test cultures.

After 5 days of culture duration a dramatic change is observed. In the field cultures the proportion of *E. coli* has increased strongly whereas the proportion of *K. pneumoniae* has subsided almost to the same extent. In addition there are certain indications that also *C. perfringens* under field conditions grows somewhat better than in the control cultures.

TABLE 5

Influence of a static electro field on the composition and the growth of a mixed bacteria culture

| Time (d) | Culture flask[a] | Total log cfu/ml[b] | E. coli | K. pneumoniae | P. aeruginosa | S. aureus | S. pyogenes | B. subtilis | C. perfringens |
|---|---|---|---|---|---|---|---|---|---|
| 0 | F1 | 7.05 | 17 | 26 | 5 | 1 | 1 | 42 | 8 |
|   | F2 | 6.98 | 17 | 20 | 4 | 1 | n.d. | 59 | n.d. |
|   | C1 | 6.97 | 14 | 28 | 2 | 1 | <1 | 43 | 12 |
|   | C2 | 6.94 | 24 | 35 | 2 | 2 | n.d. | 37 | n.d. |
| 1 | F1 | 9.20 | 29 | 17 | 13 | <1 | 0 | 40 | 1 |
|   | F2 | 9.21 | 28 | 14 | 9 | <1 | 0 | 48 | 1 |
|   | C1 | 9.14 | 37 | 18 | 6 | <1 | 0 | 38 | 1 |
|   | C2 | 9.21 | 40 | 19 | 5 | <1 | 0 | 35 | 1 |
| 2 | F1 | 9.08 | 15 | 15 | <1 | <1 | 0 | 66 | 4 |
|   | F2 | 9.01 | 23 | 13 | <1 | <1 | 0 | 63 | <1 |
|   | C1 | 9.18 | 29 | 9 | 1 | <1 | 0 | 60 | 1 |
|   | C2 | 8.79 | 30 | 5 | 1 | <1 | 0 | 63 | <1 |
| 5 | F1 | 8.39 | 64 | 3 | 2 | 14 | 0 | 15 | 2 |
|   | F2 | 8.35 | 51 | 5 | 2 | 17 | 0 | 11 | 2 |
|   | C1 | 8.24 | 62 | 2 | 2 | 23 | 0 | 10 | 1 |
|   | C2 | 8.16 | 70 | 3 | 3 | 12 | 0 | 11 | 2 |
| 6 | F1 | 8.17 | 66 | 4 | 8 | <1 | 0 | 19 | 3 |
|   | F2 | 8.27 | 67 | 6 | 5 | <1 | 0 | 17 | 4 |
|   | C1 | 8.18 | 3 | 74 | 4 | <1 | 0 | 15 | 3 |
|   | C2 | 8.13 | 3 | 78 | 5 | <1 | 0 | 12 | 3 |

[a]F1/F2 Samples cultivated under field influence; C1/C2 Control cultures
[b]Total number of the different species

7. EXAMPLE

Thin layer chromatography a) A chromatography tank for thin layer chromatography (TLC) is supplied at the outside with aluminium plates which are connected to a high voltage generator (FUG HCN 14-12500). The chromatography tank so forms the dielectricum of condenser. The plates are charged with a rectified voltage of 9,000 V, so that an electric field strength of 2,670 V/cm is effective between the plates. The tank is treated in usual manner with the eluent and the TLC-plates developed therein. 10 μl test stain mixture (lipophile) according to Stahl (Merck Art. Nr. 9353) are added to silica gel plates [(60 F 254 Muck) Nr. 5717 (5×20 cm)] and developed in carbon tetrachloride (Merck Art. Nr. 2209 Urasol) as eluent. Each one such plate is developed in this apparatus and parallel thereto another plate in a normal tank of the same size without electro field. The chromatograms developed are compared:

| Stain | $R_f$ values | |
|---|---|---|
| | without e-field | with e-field |
| 1 | 0 | 0 |
| 2 | 0,066 | 0,016 |
| 3 | 0,133 | 0,166 |
| 4 | 0,433 | 0,216 |
| 5 | 0,483 | 0,233 |
| 6 | 0,866 | 0,483 |
| height of rise of the eluent | 7,6 | 9,1 | b) 10 µl of test stain mixture (hydrophile) (Merck Art. Nr. 9352) are added to silica gel plates (60 F 254 Merck) Nr. 5717 (5×20 cm) in a manner known per se and developed in methanol/water 1:1 as eluent. Each one such plate is developed in the apparatus described and parallel thereto another plate in a normal tank of the same size without electro field. The chromatograms obtained are compared.

| Stain | $R_f$ values | |
|---|---|---|
| | without e-field | with e-field |
| 1 | 0,734 | 0,730 |
| 2 | 0,823 | 0,827 |
| 3 | 0,911 | 0,962 |
| height of rise of the eluent | 5,3 | 8,4 |

In both cases the diffusion speed of the eluent is increased. The significant polarity of the methanol appears to be the reason for the particularly distinct effect at the polar eluent.

I claim:

1. A process for isolating a secondary metabolite produced by an electrostatic field induced stress variant of halobacteria comprising:
   (a) suspending halobacteria in a suitable culture medium;
   (b) exposing the halobacteria to a static electro field;
   (c) continuing cultivation until the variant is formed, stabilized and produces secondary metabolites; and
   (d) isolating secondary metabolites from the culture medium or a lysate of the halobacteria.

2. The process of claim 1 in which the static electro field is between 1 V/cm and 10,000 V/cm.

3. The process of claim 1 in which the halobacterium strain is *Halobacterium halobium*.

4. The process of claim 1 in which the secondary metabolites are chosen from the group consisting of bacteriorhodopsin and carotenoids.

5. The process of claim 1 further comprising:
   (a) centrifuging the culture medium containing the variant of the halobacterium;
   (b) decanting the culture medium; and
   (c) solubilizing the pellet of bacteria in distilled or demineralized water.

6. A process for stabilizing an electrostatic field induced stress variant of halobacteria which produces bacteriorhodopsin and/or carotenoids as secondary metabolites comprising:
   a) introducing the halobacteria into a suitable culture medium;
   b) exposing the halobacteria to an electrostatic field; and
   c) continuing cultivation until said bacteriorhodopsin and/or carotenoids producing form of halobacteria is formed and produces bacteriorhodopsin and/or carotenoids as secondary metabolites.

7. The process of claim 6 in which the secondary metabolites produced are carotenoids.

8. A process for isolating bacteriorhodopsin and/or carotenoids produced as secondary metabolites by an electrostatic field induced stress variant of halobacteria comprising:
   a) suspending halobacteria in a suitable culture medium;
   b) exposing the halobacteria to an electrostatic field;
   c) continuing cultivation until the bacteriorhodopsin and/or carotenoids are produced as secondary metabolites; and
   d) isolating said bacteriorhodopsin and/or carotenoids from the culture medium or a lysate of the halobacteria.

9. The process of claim 8 in which the electrostatic field is between 1 V/cm and 10,000 V/cm.

10. The process of claim 8 in which the halobacterium strain is *Halobacterium halobium*.

11. The process of claim 8 further comprising:
   a) centrifuging the culture medium containing the variant of the halobacterium;
   b) decanting the culture medium; and
   c) solubilizing the pellet of bacteria in distilled or demineralized water.

* * * * *